United States Patent
Fung et al.

(10) Patent No.: US 6,979,756 B2
(45) Date of Patent: Dec. 27, 2005

(54) HEAT TREATING A MOLECULAR SIEVE AND CATALYST

(75) Inventors: Shun C. Fung, Bridgewater, NJ (US); Marcel J. G. Janssen, Kessel Lo (BE); Stephen N. Vaughn, Kingwood, TX (US); Machteld M. Mertens, Boortmeerbeek (BE); Albert Edward Schweizer, Midland, MI (US); Cornelius W. M. Van Oorschot, Brasschaat (BE); Luc R. M. Martens, Meise (BE); Richard B. Hall, Whitehouse Station, NJ (US); Wilfried J. Mortier, Kessello (BE); Ronald G. Searle, Houston, TX (US); Yi-Gang Xiong, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 10/281,645

(22) Filed: Oct. 28, 2002

(65) Prior Publication Data

US 2003/0055304 A1 Mar. 20, 2003

Related U.S. Application Data

(60) Division of application No. 09/929,949, filed on Aug. 15, 2002, now Pat. No. 6,503,863, which is a continuation-in-part of application No. 09/399,675, filed on Sep. 21, 1999, now Pat. No. 6,395,674.
(60) Provisional application No. 60/137,997, filed on Jun. 7, 1999.

(51) Int. Cl.$^7$ .............................. C07C 1/02; C07C 1/20
(52) U.S. Cl. ...................... 585/640; 585/638; 585/639
(58) Field of Search ................................. 585/638, 639, 585/640

(56) References Cited

U.S. PATENT DOCUMENTS

| | | | | |
|---|---|---|---|---|
| 4,302,565 A | * | 11/1981 | Goeke et al. | .................. 526/88 |
| 4,681,864 A | * | 7/1987 | Edwards et al. | ............... 502/63 |

OTHER PUBLICATIONS

Briend et al., "INfluence of the choice of the Template on the Short- and Long-Term Stability of SAPO-34 Zeolite", J. Phys. Chem. pp. 8270-8276, 1995. (No month available).*

* cited by examiner

*Primary Examiner*—Elizabeth D. Wood
(74) *Attorney, Agent, or Firm*—Jaimes Sher; Stephen D. Prodnuk

(57) ABSTRACT

Disclosed is a method of heat treating a molecular sieve. The method comprises providing a template-containing molecular sieve, heating the molecular sieve under conditions effective to remove a portion of the template from the molecular sieve, and cooling the heated molecular sieve to leave an amount of template effective to cover catalytic sites within the molecular sieve. A catalyst composition is also provided which comprises a molecular sieve having a microporous structure and a binder, wherein between 10 and 90 vol % of the microporous structure is occupied by a material, the material comprising a template or a carbonaceous residue of a template, and the catalyst composition exhibits a Davison Index of not greater than 30.

23 Claims, 5 Drawing Sheets

HEAT TREATING A MOLECULAR SIEVE AND CATALYST

This Application is a Division of U.S. Application Ser. No. 09/929,949, filed Aug. 15, 2002, now U.S. Pat. No. 6,503,863, which is a Continuation-in-Part of U.S. application Ser. No. 09/399,675, filed Sep. 21, 1999, now U.S. Pat. No. 6,395,674, which claims priority to U.S. Provisional Application No. 60/137,997, filed Jun. 7, 1999 and entitled "Method of Heat Treating a Molecular Sieve and Catalyst."

FIELD OF THE INVENTION

This invention relates to a method of heat treating a molecular sieve material and its corresponding catalyst composition. In particular, this invention relates to a method of heat treating a crystalline molecular sieve to provide hardness and greater olefin selectivity yet resist catalyst deactivation.

BACKGROUND OF THE INVENTION

A molecular sieve is generally a microporous structure composed of either crystalline aluminosilicate, chemically similar to clays and feldspars and belonging to a class of materials known as zeolites, or crystalline aluminophosphates derived from mixtures containing an organic amine or quaternary ammonium salt, or crystalline silicoaluminophosphates which are made by hydrothermal crystallization from a reaction mixture comprising reactive sources of silica, alumina and phosphate. Molecular sieves have a variety of uses. They can be used to dry gases and liquids; for selective molecular separation based on size and polar properties; as ion-exchangers; as catalysts in cracking, hydrocracking, disproportionation, alkylation, isomerization, oxidation, and conversion of oxygenates to hydrocarbons; as chemical carriers; in gas chromatography; and in the petroleum industry to remove normal paraffins from distillates.

Molecular sieves are manufactured by reacting a mixture of several chemical components. One of the components used in the reaction process is a template, although more than one template can be used. The templates are used to form channels or tunnel like structures (also called a microporous structure) within the composition. When the template is removed, an open microporous structure is left behind in which chemical compositions can enter, as long as the chemical compositions are small enough to be able to fit inside the tunnels. Thus a molecular sieve acts to sieve or screen out large molecules from entering a molecular pore structure.

Molecular sieves are particularly desirable for use as catalytic agents. The molecular sieves that act as catalysts have catalytic sites within their microporous structures. Once the template is removed, a chemical feedstock that is small enough to enter into the tunnels can come into contact with a catalytic site, react to form a product, and the product can leave the molecular sieve through any number of the tunnels or pores as long as the product has not become too large to pass through the structure. The pore sizes typically range from around 2 to 10 angstroms in many catalytic molecular sieves.

Template material can be removed from the framework of a molecular sieve by a variety of methods. A preferred method, however, is by calcining or heat treating in an oxygen environment, since calcining under appropriate conditions brings the additional advantage of hardening the molecular sieve. Once the molecular sieve is hardened, it can be more readily transported or more effectively blended with other materials.

U.S. Pat. No. 5,174,976 discloses one method of calcining a molecular sieve material in order to remove the template material. The method includes the steps of heating a crystalline [metallo]aluminophosphate composition to a calcination temperature at a rate no greater than 10° C. per minute with a high flow rate of a non-oxidizing gas, e.g., nitrogen, and thereafter with an oxygen-containing gas, e.g. air, at high gas flow rates, e.g., 100 to 400 cc/minute/gram. Calcination temperature is described as ranging from 100–600° C.

In U.S. Pat. No. 4,681,864, it is disclosed, however, that calcination of SAPO-37 molecular sieve compositions to remove the template material leaves a structure which is sensitive to contact with moisture. A method of removing template in order to avoid the moisture problem is suggested. Specifically, the method involves preparing a SAPO-37 molecular sieve with a template, and leaving the entire template in place for storage purposes. The molecular sieve is stated to contain an organic template in its pore structure in amounts ranging from 1 to 50% by weight of the molecular sieve, with an inorganic oxide matrix component such as silica, alumina, silica-alumina gels and sols, clay, and mixtures thereof. The entire template is removed by placing the molecular sieve in a catalytic cracking unit at 400–600° C.

Methods which are conventionally used to remove template material either fail to provide adequate protection against contact with moisture or fail to sufficiently harden the catalyst material so that it can be transported from one location to another with little physical damage. In general, it even appears that moisture damage is not a generally recognized problem. This is suggested, for example, by *Hawley's Condensed Chemical Dictionary*, Thirteenth Edition, Von Nostrand Reinhold, 1997, where it is stated that one characteristic of the molecular sieve materials is their ability to undergo dehydration with little or no change in crystalline structure. Nevertheless, even the few methods that have been suggested for providing protection of specific molecular sieve compositions do not provide a product that would be hard enough to withstand many of the physical tortures encountered during transportation, much less the physical tortures that would be encountered during actual use. Therefore, there is a need to provide molecular sieves that are effectively protected from damage due to contact with moisture and from damage due to physical contact.

SUMMARY OF THE INVENTION

In order to overcome problems related to protecting molecular sieves from damage due to contact with moisture and damage due to physical contact, this invention provides a method of heat treating a molecular sieve comprising providing a molecular sieve containing a template within a microporous structure, heating the molecular sieve under conditions effective to remove a portion of the template from the microporous structure, and cooling the heated molecular sieve to leave an amount of template or degradation product thereof effective to cover catalytic sites within the microporous structure. In another embodiment there is provided a method of making an olefin product from an oxygenate feedstock comprising, heating a molecular sieve containing a template within a microporous structure under conditions effective to remove a portion of the template from the microporous structure, cooling the heated molecular sieve to leave an amount of the template or degradation product thereof (i.e., a carbonaceous residue of a template) effective to cover catalytic sites within the molecular sieve, and contacting the molecular sieve with the oxygenate feedstock under conditions effective to convert the oxygenate feedstock to an olefin product. Preferably, the heated molecular sieve is cooled to below 100° C., preferably, below 80° C., preferably to ambient. The molecular sieve or a catalyst containing the molecular sieve can be stored or transported at the cooled conditions with relative ease. Under the cooled conditions storage or maintenance can be acceptably tolerated for at least 12 hours, preferably at least 2 weeks and most preferably at least 2 months. After storing or transporting, the molecular sieve or catalyst can be calcined to activate the catalytic sites prior to contact with the oxygenate feedstock.

In a preferred embodiment, the crystalline molecular sieve is selected from the group consisting of zeolites, tectosilicates, tetrahedral aluminophosphates and tetrahedral silicoaluminophosphates. Preferably, the crystalline molecular sieve is a crystalline silicoaluminophosphate molecular sieve, and the silicoaluminophosphate molecular sieve is preferably selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, and mixtures thereof.

Preferably, the molecular sieve is mixed within a catalyst composition comprising a binder. It is also preferred that heating is effective to provide a catalyst composition having a Davison Index of not greater than 30, more preferably not greater than 20, most preferably not greater than 10.

In yet another preferred embodiment, the template is selected from the group consisting of tetraethyl ammonium salt, cyclopentylamine, aminomethyl cyclohexane, piperidine, triethylamine, cyclohexylamine, tri-ethyl hydroxyethylamine, morpholine, dipropylamine, pyridine, isopropylamine and mixtures thereof.

A catalyst composition is also provided which comprises a molecular sieve having a microporous structure and a binder, wherein between 10 and 90 vol %, preferably between 20 and 80 vol %, more preferably between 30 and 70 vol %, of the microporous structure is occupied by a material, the material comprising a template or a or a heat degraded product thereof. Preferably, the catalyst composition exhibits a Davison Index of not greater than 30.

BRIEF DESCRIPTION OF THE DRAWINGS

The present invention will be better understood by reference to the Detailed Description of the Invention when taken together with the attached drawings, wherein.

DETAILED DESCRIPTION OF THE INVENTION

Figure 1:
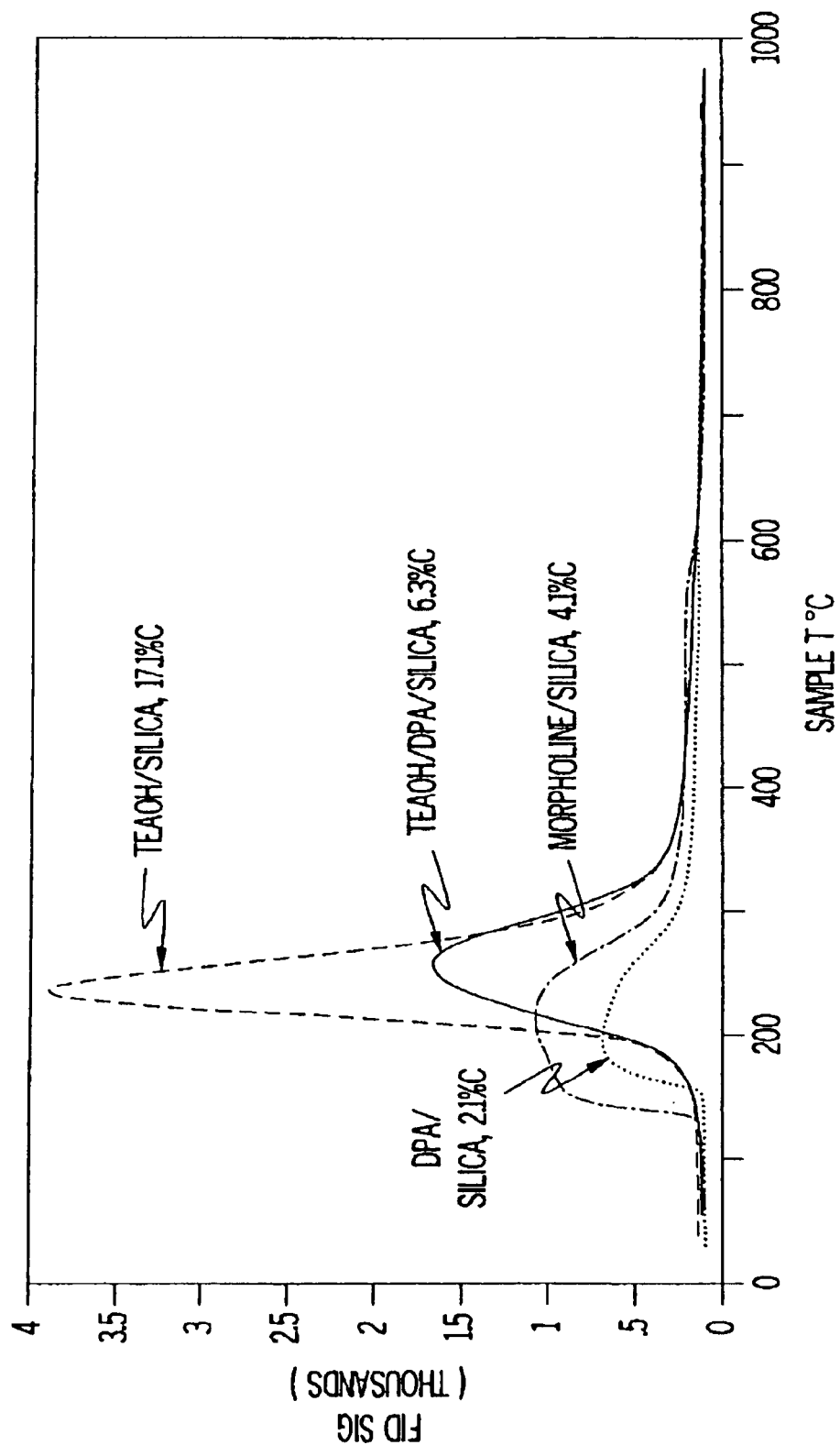
FIG. 1 shows the temperature-programmed-oxidation (TPO—1% $O_2$ in helium) spectra of TEAOH, DPA, mixed TEAOH/DPA, and morpholine deposited on high surface area silica.

The molecular sieve of this invention is protected against possible damage due to contact by moisture. In addition, the molecular sieve is in a hardened form such that there is provided effective protection against physical damage during transportation, shipping, storing or subsequent use in an operating system.

In a preferred embodiment the molecular sieve is capable of functioning as a catalyst. Preferably, the molecular sieve is selected from the group consisting of zeolites, tectosilicates, tetrahedral aluminophosphates (ALPOs) and tetrahedral silicoaluminophosphates (SAPOs). In a more preferred embodiment, the molecular sieve is a silicoaluminophosphate.

Silicoaluminophosphate molecular sieves generally comprise a three-dimensional microporous crystal framework structure of $[SiO_2]$, $[AlO_2]$ and $[PO_2]$ tetrahedral units. The way Si is incorporated into the structure can be determined by $^{29}Si$ MAS NMR. See Blackwell and Patton, J. Phys. Chem., 92, 3965 (1988). The desired SAPO molecular sieves will exhibit one or more peaks in the $^{29}Si$ MAS NMR, with a chemical shift $\sigma(Si)$ in the range of −88 to −96 ppm and with a combined peak area in that range of at least 20% of the total peak area of all peaks with a chemical shift $\sigma(Si)$ in the range of −88 ppm to −115 ppm, where the $\sigma(Si)$ chemical shifts refer to external tetramethylsilane (TMS).

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms, more preferably from 4.0 to 5.0 angstroms. These pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +3. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve structure can also be interspersed with the SAPO molecular sieves. Aluminophosphate molecular sieves are crystalline microporous oxides which can have an AlPO$_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-31, ALPO-34, ALPO-36, ALPO-37, and ALPO-46.

The ALPOs can also include a metal subtituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophospate molecular sieve compositions. Members of this class and their preparation are described in U.S. Pat. No. 4,567,029, incorporated herein by reference in its entirety.

The metal containing ALPOs have a three-dimensional microporous crystal framework structure of MO$_2$, AlO$_2$ and PO$_2$ tetrahedral units. These as manufactured structures (which contain template prior to calcination) can be represented by empirical chemical composition, on an anhydrous basis, as:

mR: (M$_x$Al$_y$P$_z$)O$_2$ wherein "R" represents at least one organic templating agent present in the intracrystalline pore system; "m" represents the moles of "R" present per mole of (M$_x$Al$_y$P$_z$)O$_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

The reaction mixture can contain one or more templates. Templates are structure directing agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

Although not necessary, it is preferable that the templates of this invention have a multimodal decomposition profile, meaning that the decomposition of the template does not exhibit a single, sharp peak as monitored by a flame ionization detector (FID). Examples include templates which have more than one peak as monitored by FID, as well as templates which have a more or less flat curve (i.e., not a single, sharp peak) as monitored by FID. The advantage of a template having this type of decomposition profile is that the "as manufactured" molecular sieve can be heated to harden the material, yet heating can be safely stopped such that a portion of the template, or at least the template's heat decomposed product, can be left within the molecular sieve to protect the framework from structural damage by moisture. The existence of a multimodal decomposition profile can be determined by using a temperature-programmed-oxidation (TPO) technique. The advantage of using a template or template mixture having a multimodal decomposition profile is that heat treatment can be controlled over a wider range of temperatures compared to a template with a sharp decomposition profile. Nevertheless, a template having a sharp decomposition profile can exhibit a flatter decomposition profile when heat treated under appropriate conditions, preferably under an oxygen depleted environment.

In the TPO technique, template-containing sieve or catalyst is loaded into a quartz reactor, gas is injected into the reactor (preferably 1% $O_2$ in helium or helium with essentially no $O_2$), and the reactor is heated at a constant rate of increase. The gas exiting the quartz reactor is directed to a methanator, which contains a ruthenium catalyst, and converts products, including CO and $CO_2$, produced during template decomposition to $CH_4$. The $CH_4$ production rate is continuously monitored with a flame ionization detector (FID). Details of this technique have been reported in S. C. Fung and C. A. Querini, *J. Cat.*, 138, 240 (1992), and C. A. Querini and S. C. Fung, *J. Cat.*, 141, 389 (1993), the descriptions of each being fully incorporated herein by reference.

The multimodal decomposition profile can be essentially flat at its maximum value or it can have two or more distinct peaks. A decomposition profile having at least two distinct peaks is particularly preferred. Preferably the profile at the approximate maximum value will extend over at least about 200° C. before the template is completely removed, more preferably at least 250° C. In other words, the profile preferably will have a first peak followed by at least one peak, and at least two of the peaks will occur over a range of at least 200° C., more preferably at least 250° C.

In this invention, it is important to heat the molecular sieve or catalyst composition to sufficiently harden the material, yet leave enough of the template or its residue within the framework of the molecular sieve to cover internal catalytic sites. That is, it is important to harden the molecular sieve or catalyst composition and protect catalytic sites within the molecular sieve by leaving sufficient template or carbonaceous material derived from the template to block contact of the sites with water molecules. Preferably, after heating the as manufactured molecular sieve, no more than 70 wt % of the template will be removed, preferably no more than 50 wt % will be removed, more preferably no more than 35 wt % of the carbonaceous material of the template will be removed, and most preferably no more than 20 wt % of the carbonaceous material will be removed.

Techniques for measuring the weight percent of template or a carbonaceous heat degradation product of a template within the microporous structure of a molecular sieve are known to those of ordinary skill in the art. A preferred technique is temperature-programmed-oxidation (TPO). In the preferred TPO technique, each material is evaluated by loading 0.005 gram of the template-containing silica material into a quartz reactor. Helium containing 1% $O_2$ (partial pressure of 1 kPa) is injected into a quartz reactor at a rate of 63 cc/min. Gas exiting the quartz reactor is preferably directed to a methanator, containing a ruthenium catalyst, to convert compositions produced during template decomposition to $CH_4$. The $CH_4$ production rate can be continuously monitored with a flame ionization detector (FID). To determine weight percent carbon from the TPO spectra, a calibration should be carried out. This is done by sending a known amount of $CO_2$ gas as a pulse to the methanator using the same carrier gas and carrier gas flow rate as in the TPO experiment. This provides a peak in the FID signal from which a calibration factor is determined, i.e., the amount of carbon per unit area. The weight percent of carbon, i.e., the amount of template in the microporous structure, is calculated by multiplying the spectral area from the helium step by the calibration factor.

In a preferred embodiment, the heat treated material will comprise at least one molecular sieve having catalytic sites and the molecular sieve is admixed (blended) with other materials. In this blended form, the overall composition is typically referred to as a molecular sieve catalyst.

Materials which can be blended with the molecular sieve can be various inert or catalytically active materials, or various binder materials. These materials include compositions such as kaolin and other clays, various forms of rare earth metals, other non-zeolite catalyst components, zeolite catalyst components, alumina or alumina sol, titania, zirconia, quartz, silica or silica or silica sol, and mixtures thereof. These components are also effective in reducing overall catalyst cost, acting as a thermal sink to assist in heat shielding the catalyst during regeneration, densifying the catalyst and increasing catalyst strength. The amount of molecular sieve which is contained in the final molecular sieve catalyst product ranges from 10 to 90 weight percent of the total catalyst, preferably 30 to 70 weight percent of the total catalyst.

In a preferred embodiment, the heat treated material is a molecular sieve catalyst comprising a molecular sieve having a microporous structure with catalyst sites therein and a binder. The microporous structure is occupied by between 10 and 90 vol % of at least one template or a heat degradation product thereof, preferably 20 and 80 vol % of at least one template or a heat degradation product thereof, and more preferably between 30 and 70 vol % of at least one template or a heat degradation product thereof.

One way in which the amount of template- or degradation product within the microporous structure of a molecular sieve can be determined is by comparing the methanol adsorption capacity of the partially detemplated molecular sieve to its fully detemplated counterpart. The ratio of the methanol adsorption capacity of the partially detemplated molecular sieve to the methanol adsorption capacity of the fully detemplated counterpart will indicate the void space in the partially detemplated template. Techniques for measuring methanol adsorption capacity are known to those of ordinary skill in the art. In a preferred technique, about 5 mg of sample is introduced into a thermogravimetric analyzer (TGA). The sample is subjected to a heat treatment process, which includes: (1) heating from room temperature to 150° C., with a heat up rate of 10° C./min. in nitrogen; (2) holding at 150° C. for 60 min. (to remove any entrapped moisture, but not degrade template further); and cooling to 30° C. in nitrogen. After the sample has reached 30° C., methanol containing nitrogen is flowed into the TGA at methanol partial pressure of 0.09 atm. The sample is contacted with this nitrogen/methanol mixture for 180 minutes. The methanol adsorption capacity is the weight percent weight increase after the 180 minutes contact with the methanol vapor.

The hardness of the sieve composition can be determined by measuring attrition resistance using the well known Jet Cup Attrition Method. This is also commonly referred to as the Davison Attrition Index or Davison Index (DI). See, e.g., U.S. Pat. Nos. 5,547,564 and 5,364,516. The molecular sieve or catalyst composition of this invention is desirably hard enough to provide protection against physical damage during transportation or storing, preferably hard enough to be introduced into a manufacturing unit to provide protection against physical damage during operation. It is preferred in this invention that the molecular sieve or catalyst composition exhibits a Davison Index of not greater than 30, preferably not greater than 20, more preferably not greater than 10. In general, the lower the Davison Index, the harder the composition.

In this invention, the Davison Index is determined as follows:

A sample of molecular sieve with binder material is analyzed to determine the 0 to 20 micron size content. The sample is then subjected to a 20 minute test in a Fluid Catalyst Attrition Apparatus using a hardened steel jet cup having a precision bored orifice. An air flow of 18 liters per minute is used. The Davison Index is calculated as $$\text{Davison Index} = \frac{\text{wt. 0-20 micron material formed during test}}{\text{wt. original 20}^+ \text{ micron fraction}}$$

It is preferred that the molecular sieve be mixed with at least a binder material and heated under conditions effective to obtain a Davison Index of not greater than 30, preferably not greater than 20, more preferably not greater than 10. This will provide sufficient hardness so that the sieve or catalyst can be safely transported, yet leave sufficient amount of template or template residue within the microporous structure of the sieve to protect against degradation of active sites by contact with moisture.

A preferred hardening temperature is in the range of between 200° C. and 800° C., more preferably in the range of between 300° C. and 700° C., most preferably in the range of between 400° C. and 650° C. The upper temperature limit will be determined by the amount of template or template residue that is to desirably remain in the microporous structure after this initial heating. Heat treatment can be carried out in an inert gas or an oxygen containing gas (e.g., air) as long as these two conditions are satisfied.

Heat treatment is preferably carried out in an oxygen depleted environment. An oxygen depleted environment is preferred, since this type of environment will typically extend the decomposition profile of the template. This means that an oxygen depleted environment will extend the temperature range over which the template will be fully decomposed. This will provide an advantage of being able to increase the temperature at which the method can be carried out. The benefit is that additional mechanical strength can be gained, while keeping sufficient template within the molecular pore structure to guard against structural damage by contact with water molecules.

The oxygen depleted environment can be provided by using a treat gas having an oxygen partial pressure of less than 21 kPa, preferably less than 1 kPa, more preferably less than 0.1 kPa and most preferably less than 0.01 kPa. The treat gas is preferably selected from the group consisting of nitrogen, helium, neon, argon, CO and $CO_2$.

Although it is preferred to use a multimodal template in this invention it is not necessary, since use of the TPO technique will enable one to determine the temperature decomposition profile for any template material. Even a template which exhibits a sharp peak in its temperature decomposition profile can be used as long as the heat treatment employs a temperature sufficiently high to harden the sieve material, but sufficiently low to maintain a quantity of template or carbonaceous material derived from the template in the microporous structure effective to protect from structural damage as a result of contact with water molecules. In the case where the temperature decomposition profile has a single peak, it is preferable that the heat treatment be between the peak decomposition temperature and 150° C. below the peak decomposition temperature, more preferably between the peak decomposition temperature and 100° C. below the peak decomposition temperature, most preferably between the peak decomposition temperature and 75° C. below the peak decomposition temperature. The peak decomposition temperature is defined as the temperature corresponding to the apex of the single peak temperature decomposition profile.

Once the molecular sieve or the molecular sieve contained in a binder material has been heat treated, the material is desirably sufficiently hard to transport with ease. Because the sieve contains an amount of template within the pore structure effective to protect against contact with water molecules, the sieve can also be stored for extended periods of time without undue concern for structural damage.

Prior to use in a catalytic reactor the heat treated (hardened) molecular sieve catalyst of the invention may be subjected to a second heat treatment to completely remove the remaining template from the pore structure. This second heat treatment is not necessary and in some cases it may be preferred that the catalyst be used with portions of the decomposed template still positioned in the pores of the molecular sieve. If complete removal of the template is warranted, the template can be calcined, or combusted, in the presence of an oxygen-containing gas, such as air, to remove the remaining template. The calcining step can be performed at any temperature sufficient to remove the remaining template, preferably at least 300° C. and up to 900° C., with the lower limit being determined by the amount of template or template residue that remains in the microporous structure after the initial hardening step. In other words, calcining the final template or residue removal will be accomplished by heating at a temperature higher than that during hardening.

Calcining can be preformed in situ or ex situ. In situ calcining means that complete removal of the remaining template or its decomposition product can be removed inside a reactor unit when the molecular sieve or catalyst is desired to be used as a catalyst. However, in a preferred embodiment, the template or carbonaceous material is removed ex situ. This means that it is preferred to activate the catalytic sites of the molecular sieve outside of the reactor. This is because there is less likelihood that the template material will contaminate the reaction products. This is particularly beneficial when the molecular sieve is used to convert oxygenate feed to olefin product. In cases such as these the olefin product is typically required to be very low in any nitrogen or sulfur-containing contaminants. Since template likely will contain at least some nitrogen components, it would be more desirable to remove remaining template outside the reactor. Complete template removal in the regenerator or return line from the regenerator to the reactor is acceptable.

In another embodiment of the invention the heat treated (hardened) molecular sieve catalyst is not subjected to the second, aerobic heat treatment, e.g., calcination. Instead, the molecular sieve is used in a catalytic conversion reactor, particularly a reactor used to convert methanol, after the single heat treatment, preferably where the heat treatment is carried out in a depleted oxygen environment.

The molecular sieve synthesized in accordance with the present method can be used to dry gases and liquids; for selective molecular separation based on size and polar properties; as an ion-exchanger; as a catalyst in cracking, hydrocracking, disproportionation, alkylation, isomerization, oxidation, and conversion of oxygenates to hydrocarbons; as a chemical carrier; in gas chromatography; and in the petroleum industry to remove normal paraffins from distillates. It is particularly suited for use as a catalyst in cracking, hydrocracking, disproportionation, alkylation, isomerization, oxidation, and conversion of oxygenates to hydrocarbons. Most particularly, the molecular sieve is suited for use as a catalyst in the conversion of oxygenates to hydrocarbons.

In its most preferred embodiment as a catalyst in the conversion of oxygenates to hydrocarbons, a feed containing an oxygenate is contacted in a reaction zone of a reactor apparatus with a molecular sieve catalyst at process conditions effective to produce light olefins, i.e., an effective temperature, pressure, WHSV (weight hour space velocity) and, optionally, an effective amount of diluent, correlated to produce light olefins. These conditions are described in detail below. Usually, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions. As used herein, the term reactor includes not only commercial scale reactors but also pilot sized reactor units and lab bench scale reactor units.

Olefins can generally be produced at a wide range of temperatures. An effective operating temperature range can be from about 200° C. to 700° C. At the lower end of the temperature range, the formation of the desired olefin products may become markedly slow. At the upper end of the temperature range, the process may not form an optimum amount of product. An operating temperature of at least 300° C., and up to 500° C. is preferred.

Owing to the nature of the process, it may be desirable to carry out the process of the present invention by use of the molecular sieve catalysts in a dynamic bed system or any system of a variety of transport beds rather than in a fixed bed system. It is particularly desirable to operate the reaction process at high space velocities.

The conversion of oxygenates to produce light olefins may be carried out in a variety of large scale catalytic reactors, including, but not limited to, fluid bed reactors and concurrent riser reactors as described in "Free Fall Reactor," *Fluidization Engineering*, D. Kunii and O. Levenspiel, Robert E. Krieger Publishing Co. NY, 1977, incorporated in its entirety herein by reference. Additionally, countercurrent free fall reactors may be used in the conversion process. See, for example, U.S. Pat. No. 4,068,136 and "Riser Reactor", *Fluidization and Fluid-Particle Systems*, pages 48–59, F. A. Zenz and D. F. Othmo, Reinhold Publishing Corp., NY 1960, the descriptions of which are expressly incorporated herein by reference.

Any standard commercial scale reactor system can be used, including fixed bed or moving bed systems. The commercial scale reactor systems can be operated at a weight hourly space velocity (WHSV) of from 1 hr$^{-1}$ to 1000 hr$^{-1}$. In the case of commercial scale reactors, WHSV is defined as the weight of hydrocarbon in the feed per hour per weight of silicoaluminophosphate molecular sieve content of the catalyst. The hydrocarbon content will be oxygenate and any hydrocarbon which may optionally be combined with the oxygenate. The silicoaluminophosphate molecular sieve content is intended to mean only the silicoaluminophosphate molecular sieve portion that is contained within the catalyst. This excludes components such as binders, diluents, inerts, rare earth components, etc.

It is highly desirable to operate at a temperature of at least 300° C. and a Temperature Corrected Normalized Methane Sensitivity (TCNMS) of less than about 0.016, preferably less than about 0.012, more preferably less than about 0.01. It is particularly preferred that the reaction conditions for making olefin from oxygenate comprise a WHSV of at least about 20 hr$^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T-400)/400) \times 14.84)}$$

The pressure also may vary over a wide range, including autogenous pressures. Preferred pressures are in the range of about 5 kPa to about 5 MPa, with the most preferred range being of from about 50 kPa to about 0.5 MPa. The foregoing pressures are exclusive of any oxygen depleted diluent, and thus, refer to the partial pressure of the oxygenate compounds and/or mixtures thereof with feedstock.

One or more inert diluents may be present in the feedstock, for example, in an amount of from 1 to 99 molar percent, based on the total number of moles of all feed and diluent components fed to the reaction zone (or catalyst). Typical diluents include, but are not necessarily limited to, helium, argon, nitrogen, carbon monoxide, carbon dioxide, hydrogen, water, paraffins, alkanes (especially methane, ethane, and propane), alkylenes, aromatic compounds, and mixtures thereof. The preferred diluents are water and nitrogen. Water can be injected in either liquid or vapor form.

The process may be carried out in a batch, semi-continuous or continuous fashion. The process can be conducted in a single reaction zone or a number of reaction zones arranged in series or in parallel.

The level of conversion of the oxygenates can be maintained to reduce the level of unwanted by-products. Conversion can also be maintained sufficiently high to avoid the need for commercially undesirable levels of recycling of unreacted feeds. A reduction in unwanted by-products is seen when conversion moves from 100 mol % to about 98 mol % or less. Recycling up to as much as about 50 mol % of the feed is commercially acceptable. Therefore, conversions levels which achieve both goals are from about 50 mol % to about 98 mol % and, desirably, from about 85 mol % to about 98 mol %. However, it is also acceptable to achieve conversion between 98 mol % and 100 mol % in order to simplify the recycling process. Oxygenate conversion may be maintained at this level using a number of methods familiar to persons of ordinary skill in the art. Examples include, but are not necessarily limited to, adjusting one or more of the following: the reaction temperature; pressure; flow rate (i.e., WHSV); level and degree of catalyst regeneration; amount of catalyst re-circulation; the specific reactor configuration; the feed composition; and other parameters which affect the conversion.

If regeneration is required, the molecular sieve catalyst can be continuously introduced as a moving bed to a regeneration zone where it can be regenerated, such as for example by removing carbonaceous materials or by oxidation in an oxygen-containing atmosphere. In a preferred embodiment, the catalyst is subject to a regeneration step by burning off carbonaceous deposits accumulated during the conversion reactions.

The oxygenate feedstock comprises at least one organic compound which contains at least one oxygen atom, such as aliphatic alcohols, ethers, carbonyl compounds (aldehydes, ketones, carboxylic acids, carbonates, esters and the like), and the feedstock may optionally contain at least one compound containing a halide, mercaptan, sulfide, or amine, as long as the optional components do not significantly impede the performance of the catalyst. When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols, their unsaturated counterparts and the nitrogen, halogen and sulfur analogues of such. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

This invention will be better understood with reference to the following examples, which are intended to illustrate specific embodiments within the overall scope of the invention as claimed.

EXAMPLE 1

Four different templates (TEAOH, TEAOH/DPA, DPA, and morpholine) were impregnated in silica powder by the following technique. A solution containing a calculated amount of template was added to silica powder in dropwise manner and mixed. After the desired amount of template was added, the silica powder was dried in air, then at 120° C., to remove water and solvent. The following materials were formed: (1) TEAOH/silica (containing 17.1 wt. % carbon); (2) TEAOH/DPA/silica (containing 6.3 wt. % carbon); (3) morpholine/silica (containing 4.1 wt. % carbon); and (4) DPA/silica (containing 2.1 wt. % carbon).

The dried materials were then subjected to temperature-programmed-oxidation (TPO). In the TPO technique, each material was evaluated by loading 0.005 gram of the template-containing silica material into a quartz reactor. Helium containing 1% $O_2$ (i.e., oxygen partial pressure of 1 kPa) was injected into the reactor at a rate of 63 cc/min. The gas exiting the quartz reactor was directed to a methanator, containing a ruthenium catalyst, to convert compositions produced during template decomposition to $CH_4$. The $CH_4$ production rate was continuously monitored with a flame ionization detector (FID). FIG. 1 shows the decomposition spectra of each sample. The figure indicates that templates deposited on high surface area silica give similar peak decomposition temperatures, with all peak decomposition temperatures below about 300° C.

EXAMPLE 2

Figure 2:
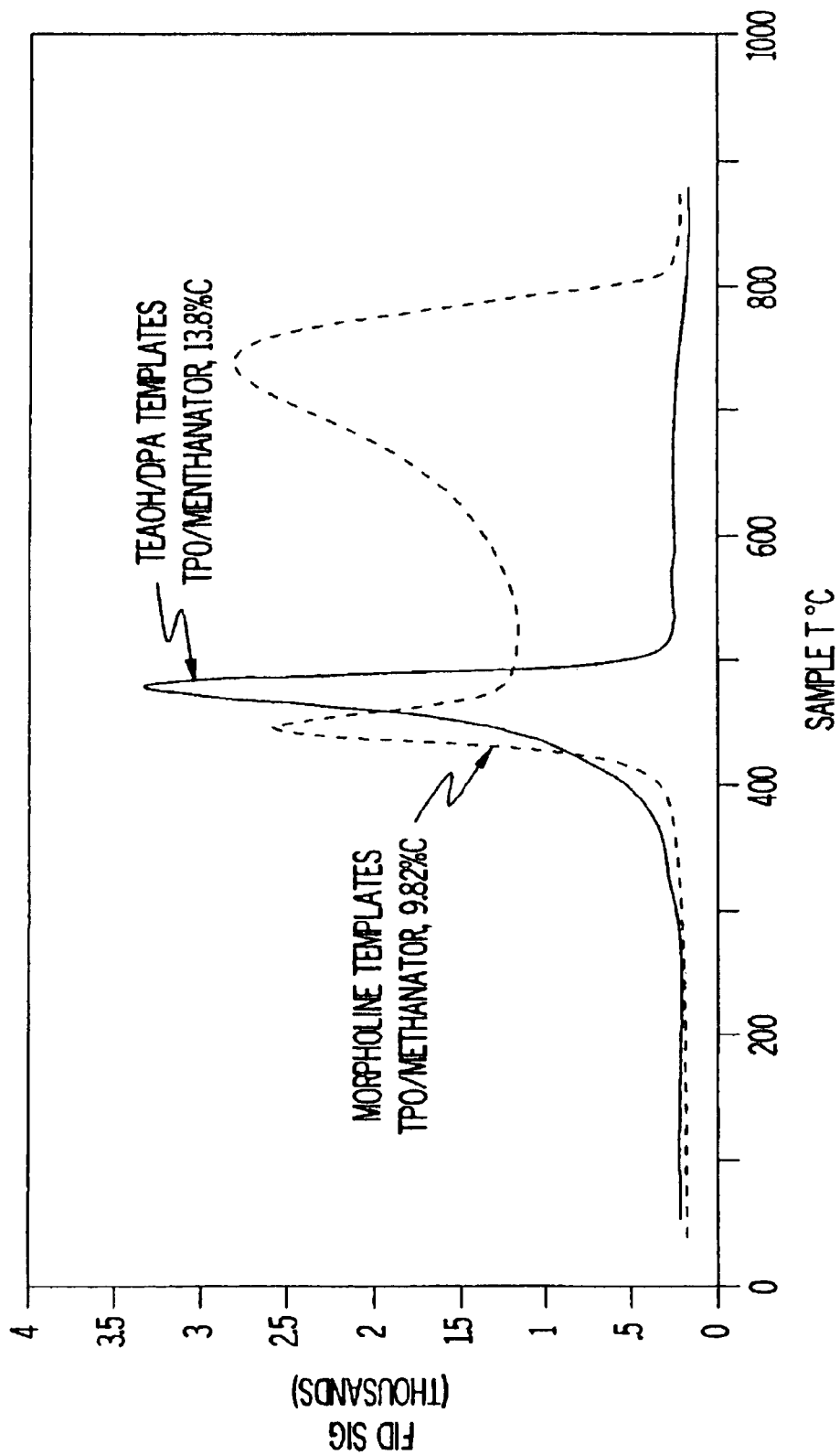
FIG. 2 shows the TPO spectra of a SAPO-34 molecular sieve having a mixed TEAOH/DPA template and a SAPO-34 molecular sieve having a morpholine template.

A sample of SAPO-34 containing TEAOH/DPA as template material (13.8 wt. % carbon in the templated material), and a sample of SAPO-34 containing morpholine as a template (9.82 wt. % carbon in the templated material) were subjected to decomposition analysis as in Example 1. FIG. 2 shows the decomposition spectra of each sample. The figure indicates that morpholine template has a multimodal decomposition profile, whereas TEAOH/DPA has a single composition peak. It is unexpected that the template decomposition temperatures of the microporous molecular sieves of this Example are substantially higher than the template decomposition temperatures of Example 1.

EXAMPLE 3

Figure 3:
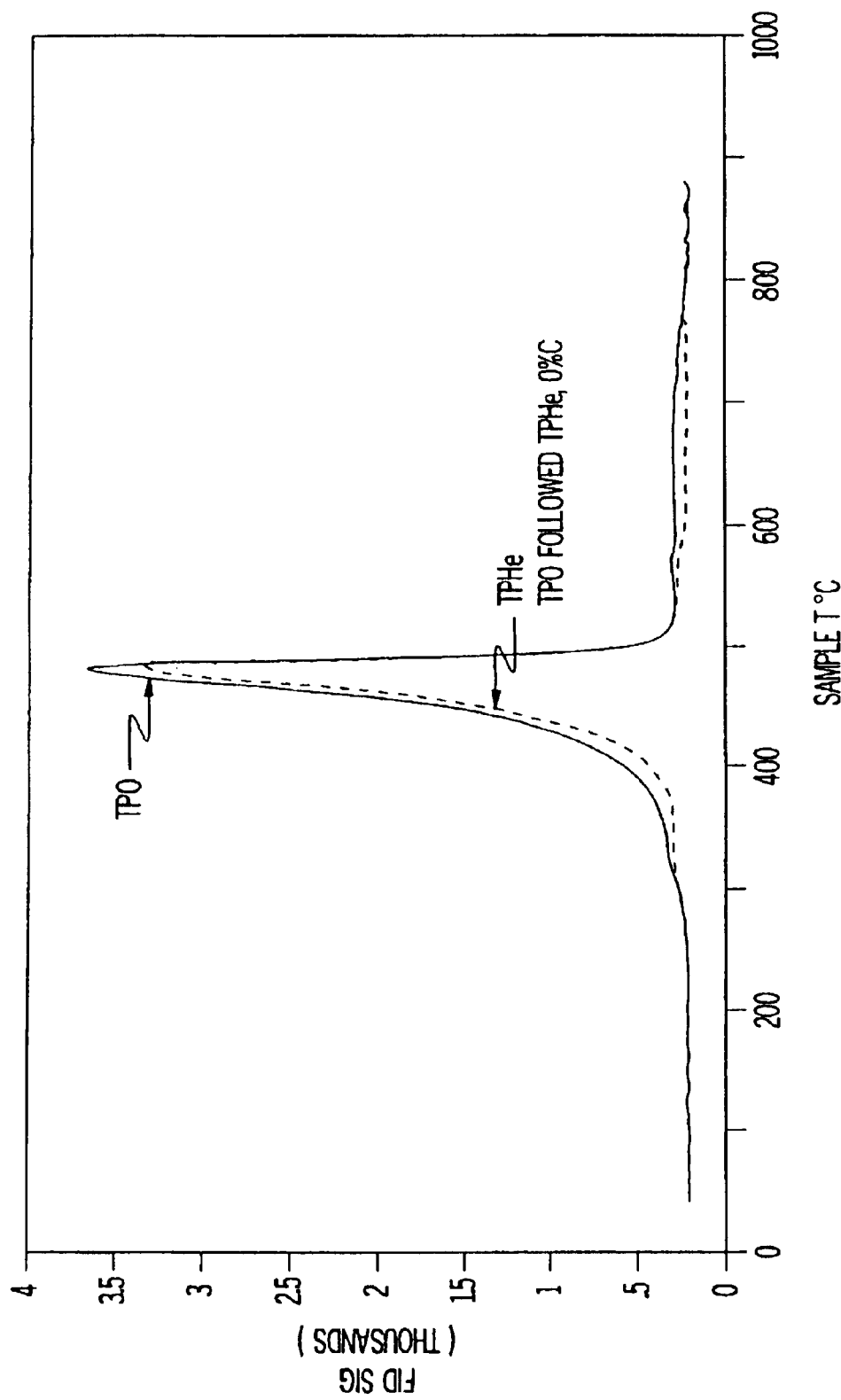
FIG. 3 shows a comparison of the TPO (oxygen in helium) and the TPO (no oxygen in helium) spectra of a SAPO-34 molecular sieve having a mixed TEAOH/DPA template.

A first sample of SAPO-34 containing TEAOH/DPA as template material was subjected to decomposition analysis as in Example 1. A second sample of SAPO-34 containing TEAOH/DPA as template material was subjected to decomposition analysis as in Example 1, except that the helium injected into the reactor contained essentially no oxygen. FIG. 3 shows the decomposition spectra of each sample. In this particular example, the reduction in oxygen content had little if any effect on extending the decomposition profile.

EXAMPLE 4

Figure 4:
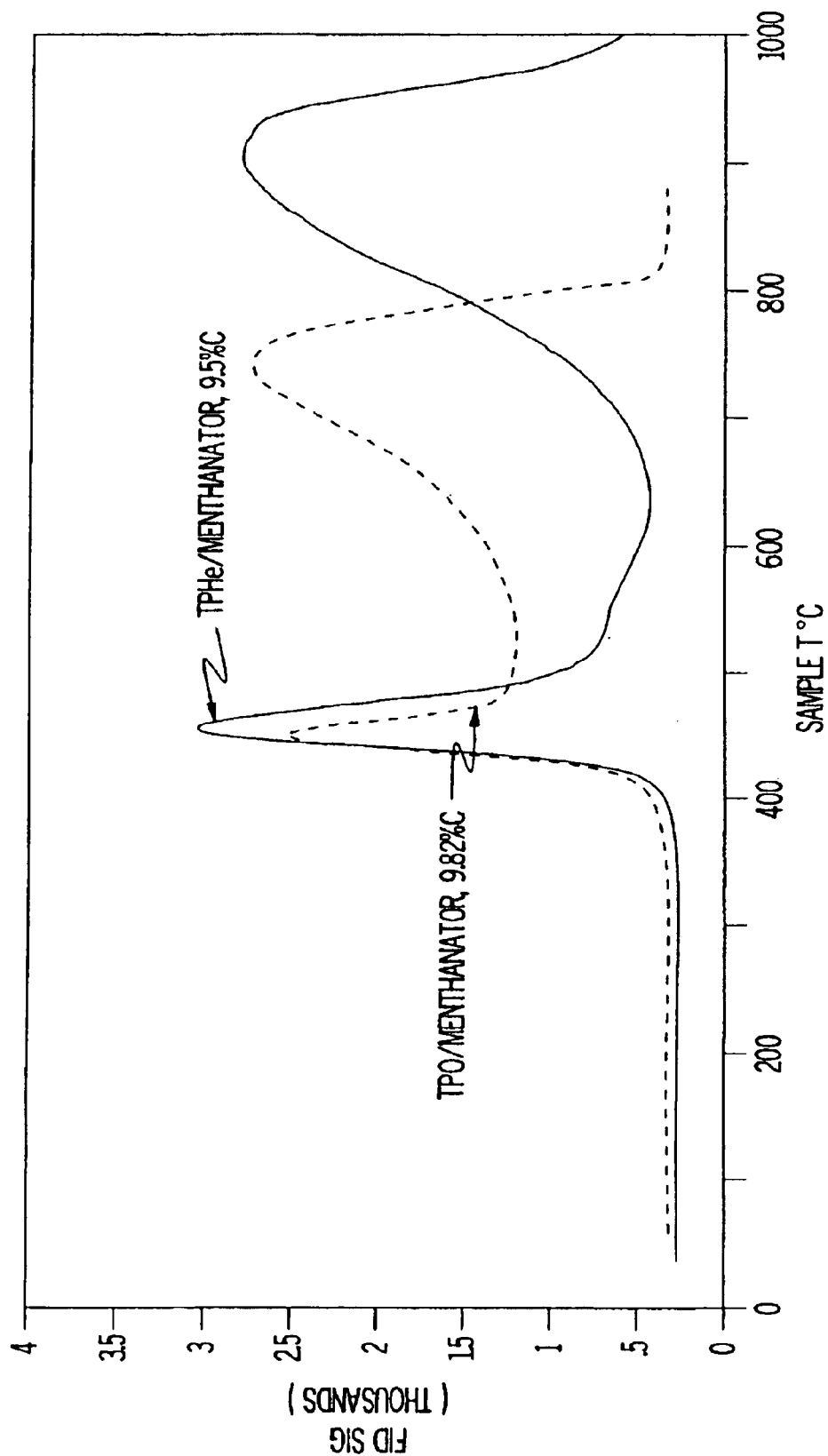
FIG. 4 shows a comparison of the TPO (oxygen in helium) and the TPO (no oxygen in helium) spectra of SAPO-34 molecular sieves having morpholine templates.

A first sample of SAPO-34 containing morpholine as template material (9.82 wt. % carbon in the templated material) was subjected to decomposition analysis as in Example 1. A second sample of SAPO-34 containing morpholine as template material (9.5 wt. % carbon in the templated material) was subjected to decomposition analysis as in Example 1, except that the helium injected into the reactor contained essentially no oxygen. FIG. 4 shows the decomposition spectra of each sample. In this particular example, the two samples contained essentially the same amount of template material and the reduction in oxygen content significantly extended the decomposition profile.

EXAMPLE 5

Figure 5:
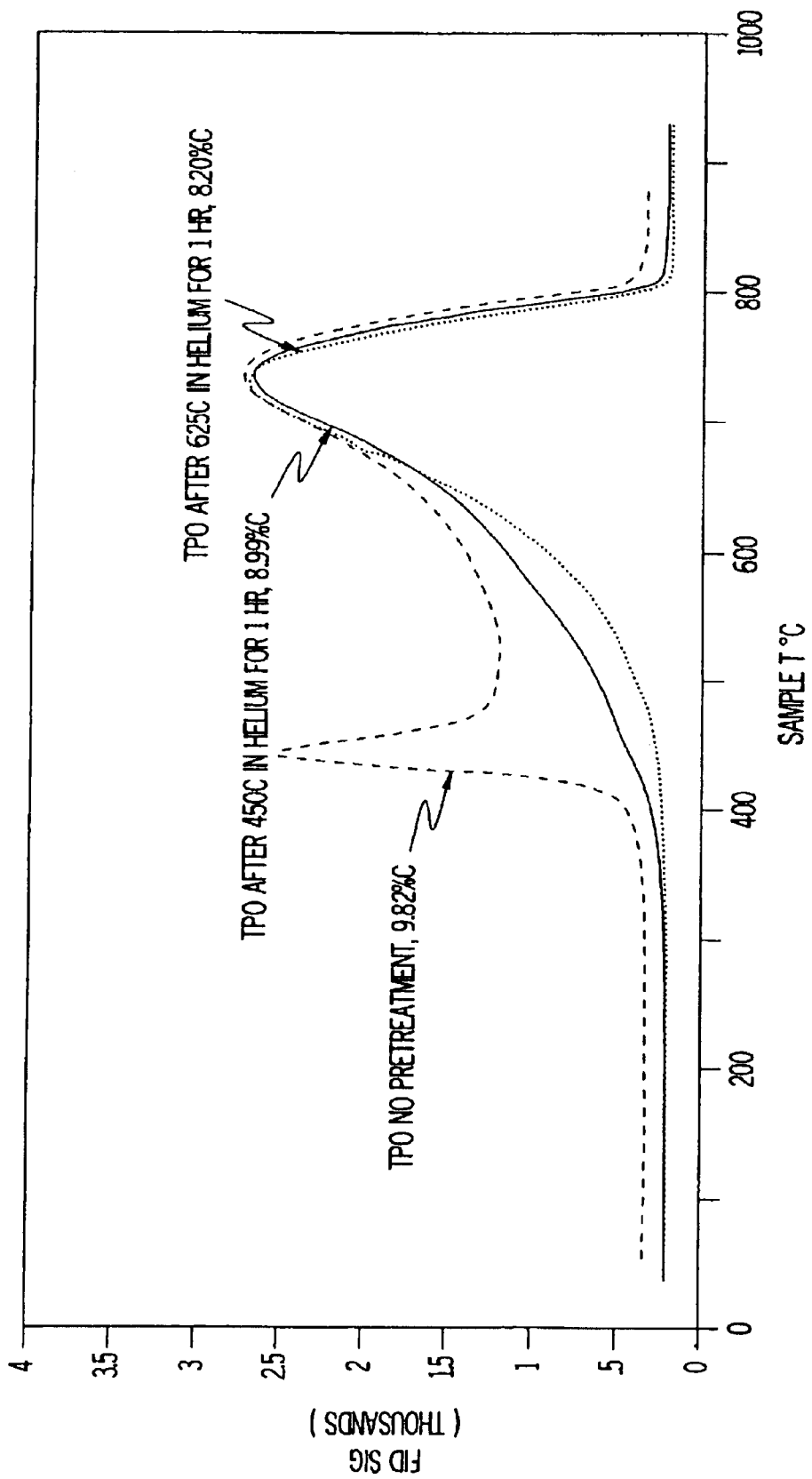
FIG. 5 shows the TPO spectra of SAPO-34 molecular sieves having a morpholine template in SAPO-34, one sample having been heat pretreated at 450° C. in helium for 1 hour, one sample having been heat pretreated at 625° C. in helium for 1 hour, and another sample having no heat pretreatment.

Three samples of SAPO-34 containing morpholine as a template material were evaluated. A first sample (containing 9.82 wt. % carbon) was subjected to decomposition analysis as in Example 1. FIG. 5 shows the decomposition profile of the sample.

A second sample was heat pretreated by heating in helium for 1 hour at 450° C. to density the material. Following heat pretreatment, the sample was subjected to decomposition analysis as in Example 1. FIG. 5 shows the decomposition profile of the sample. This profile shows that following heat pretreatment, the sample contained 8.99 wt. % carbon in the sample (about 92% of the total carbonaceous material, based on a total of 8.99 out of a total of 9.82).

A third sample was heat pretreated by heating in helium for 1 hour at 625° C. to density the material. Following heat pretreatment, the sample was subjected to decomposition analysis as in Example 1. FIG. 5 shows the decomposition profile of the sample. This profile shows that following heat pretreatment, the sample contained 8.20 wt. % carbon in the sample (about 84 wt. % of the total carbonaceous material, based on 8.2 out of a total of 9.82).

EXAMPLE 6

A catalyst composition comprising about 50% SAPO-34, the remainder being binder material, was spray dried and analyzed for hardness using the well known Jet Cup Attrition Method, i.e., the Davison Attrition Index or Davison Index (DI) method. The catalyst composition was analyzed to determine the 0 to 20 micron size content. The composition was then subjected to a 20 minute test in a Fluid Catalyst Attrition Apparatus using a hardened steel jet cup having a precision bored orifice. An air flow of 18 liters per minute was used. The Davison Index was calculated to be 65.4 (percent loss to <20 microns in 20 minutes).

EXAMPLE 7

A catalyst composition comprising about 50% SAPO-34, the remainder being binder material, was spray dried and calcined for 2 hours at 550° C. The calcined composition was analyzed for hardness using the well known Jet Cup Attrition Method as in Example 6. The Davison Index was calculated to be 7.5 (percent loss to <20 microns in 20 minutes).

EXAMPLE 8

A sample of SAPO-34 molecular sieve prepared with a morpholine template was heat treated under nitrogen for 5 hours followed by heating in air for 3 hours at 650° C. (heat up 5° C./min). The sample was then transferred to a tubular, fixed bed reactor, equipped with an on-line GC for product analysis. The reactor conditions were 450° C., 25 WHSV, 25 psig, with methanol as the feed. The sample exhibited an ethylene, propylene and propane selectivities of 23%, 32% and 19%, respectively.

EXAMPLE 9

A sample of SAPO-34 molecular sieve prepared with a morpholine template was heat treated under nitrogen for a total of about 4 hours. The temperature was programmed to increase 5° C./min until a temperature of 625° C. was achieved. The sample was then maintained at 625° C. under nitrogen for one hour. The second sample exhibited an ethylene, propylene and propane selectivities of 31%, 36% and 9%, respectively. This is an increase of 12% in light olefin selectivity and a decrease in 10% of the undesired propane over the sample of Example 8.

To understand the observed increased olefin selectivities in this Example a TPO experiment was performed. A sample of SAPO-34 prepared with a morpholine template was heat treated under nitrogen for a total of about 4 hours. The temperature was programmed to increase 5° C./min until a temperature of 625° C. was achieved. The sample was then maintained at 625° C. under nitrogen for one hour. A weight loss of only 12.9% was observed. The flow gas was then switched to air and heated at 625° C. for an additional hour; and an additional 8.7% loss in weight was observed. This data reveals that the heat treated (nitrogen) molecular sieve with the higher olefin selectivity has at least 8.7% more residual carbon in the pore structure than a sample catalyst that undergoes a subsequent heat treatment (calcination) in air.

It is to be understood that the amount of carbon contained within the pores is dependent upon the time and the temperature at which the molecular sieve is heated. Therefore, the invention is not per se directed to the temperatures and times given in the above Examples, but rather to the method of heating the molecular sieve and molecular sieve catalyst in an oxygen or oxygen depleted environment to give a molecular sieve or molecular sieve catalyst with a preferred amount of carbon or "coke" disposed within the pores.

Having now fully described this invention, it will be appreciated by those skilled in the art that the invention can be performed within a wide range of parameters within what is claimed, without departing from the spirit and scope of the invention.

What is claimed is:

1. A method of making an olefin product from an oxygenate feedstock comprising, heating a molecular sieve containing a template within a microporous structure under conditions effective to remove a portion of the template from the microporous structure, cooling the heated molecular sieve to leave an amount of the template or a degradation product thereof effective to cover catalytic sites within the microporous structure, and contacting the molecular sieve with the oxygenate feedstock under conditions effective to convert the oxygenate feedstock to an olefin product.

2. The method of claim 1, wherein the molecular sieve is selected from the group consisting of zeolites, tectosilicates, tetrahedral aluminophosphates and tetrahedral silicoaluminophosphates.

3. The method of claim 1, wherein the molecular sieve is heated in an environment having an oxygen partial pressure of less than 21 kPa.

4. The method of claim 3, wherein the molecular sieve is heated in an environment having an oxygen partial pressure of less than 1 kPa.

5. The method of claim 4, wherein the molecular sieve is heated in an environment having an oxygen partial pressure of less than 0.1 kPa.

6. The method of claim 1, wherein not more than 70 wt % of the template is removed from the molecular sieve during heating.

7. The method of claim 6, wherein not more than 50 wt % is removed from the molecular sieve during heating.

8. The method of claim 7, wherein not more than 35 wt % is removed from the molecular sieve during heating.

9. The method of claim 8, wherein not more than 20 wt % is removed from the molecular sieve during heating.

10. The method of claim 1, wherein the molecular sieve is combined with a binder and hardened upon heating.

11. The method of claim 1, wherein the molecular sieve has a pore size of less than 5 angstroms.

12. The method of claim 1, wherein the molecular sieve is provided within a catalyst composition comprising a binder.

13. The method of claim 1, wherein heating to remove a portion of the template is effective to provide a catalyst composition having a Davison index of not greater than 30.

14. The method of claim 1, wherein heating to remove a portion of the template is effective to provide a catalyst composition having a Davison index of not greater than 20.

15. The method of claim 1, wherein beating to remove a portion of the template is effective to provide a catalyst composition having a Davison index of not greater than 10.

16. The method of claim 1, wherein the molecular sieve is a crystalline silicoaluminophosphate molecular sieve.

17. The method of claim 16, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, and mixtures thereof.

18. The method of claim 17, wherein the molecular sieve is SAPO-34.

19. The method of claim 1, wherein the molecular sieve is heated at a temperature of 200 to 800° C.

20. The method of claim 1, wherein the molecular sieve is cooled to a temperature of less than 100° C.

21. The method of claim 1, wherein the template is selected from the group consisting of tetraethyl ammonium hydroxide, cyclopentylamine, aminomethyl cyclohexane, piperidine, triethylamine, cyclohexylamine, tri-ethyl hydroxyethylamine, morpholine, dipropylamine, pyridine, isopropylamine and mixtures thereof.

22. The method of claim 1, wherein the molecular sieve is heated substantially in the absence of oxygen.

23. The method of claim 1 further comprising calcining the cooled molecular sieve prior to contacting the molecular sieve with the oxygenate feedstock.

\* \* \* \* \*